US012502480B1

(12) United States Patent
Javitt

(10) Patent No.: US 12,502,480 B1
(45) Date of Patent: Dec. 23, 2025

(54) SYSTEM AND METHOD FOR ADMINISTRATION OF A SUBSTANCE

(71) Applicant: Abusarah, Inc., Wilmington, DE (US)

(72) Inventor: Daniel C. Javitt, Dobbs Ferry, NY (US)

( * ) Notice: Subject to any disclaimer, the term of this patent is extended or adjusted under 35 U.S.C. 154(b) by 0 days.

(21) Appl. No.: 19/040,893

(22) Filed: Jan. 30, 2025

(51) Int. Cl.
*A61M 5/172* (2006.01)
*G16H 20/17* (2018.01)

(52) U.S. Cl.
CPC .......... *A61M 5/1723* (2013.01); *G16H 20/17* (2018.01); *A61M 2005/1726* (2013.01)

(58) Field of Classification Search
None
See application file for complete search history.

(56) References Cited

U.S. PATENT DOCUMENTS 2,888,922 A 6/1959 Weldon
5,335,659 A 8/1994 Pologe
7,833,213 B2 11/2010 Katz
8,864,702 B2 10/2014 Chazot
9,132,228 B2 9/2015 Yan
9,849,241 B2 12/2017 Becker
9,950,112 B2 4/2018 Melker
10,537,677 B2 1/2020 Chazot
11,135,360 B1 * 10/2021 Jacobson ............... G16H 20/17
2004/0230108 A1 11/2004 Melker
2006/0136271 A1 * 6/2006 Eggers .................. G16H 40/40 600/301
2007/0010756 A1 1/2007 Viertio-Oja
2007/0088271 A1 * 4/2007 Richards ........... A61M 5/14244 604/890.1
2008/0071251 A1 * 3/2008 Moubayed ............ G16H 20/17 604/890.1
2008/0108970 A1 5/2008 Viertio-Oja
2009/0177181 A1 7/2009 Schmidt
2019/0228669 A1 7/2019 Baym
2022/0184309 A1 * 6/2022 Rosinko ................ G06F 1/3215
2022/0401956 A1 * 12/2022 Chao ................. B01L 3/502761

FOREIGN PATENT DOCUMENTS

CN 106730110 5/2017
WO 2008099356 8/2008

* cited by examiner

*Primary Examiner* — Manuel A Mendez
(74) *Attorney, Agent, or Firm* — JMB DAVIS BEN-DAVID

(57) ABSTRACT

Disclosed herein is a system for administering a substance to a patient, the system comprising a reservoir for storing the substance, an administration apparatus configured to administer the substance to the patient, a pump for directing the substance from the reservoir to the delivery mechanism, a controller configured to operate the pump, a communication unit configured to communicate with at least one server, at least one processor configured to receive data associated with patient characteristics, calculate a substance administration dose according to the data, determine a preferred substance administration process, and operate the pump to administer the substance to the patient.

10 Claims, 5 Drawing Sheets

100

SYSTEM AND METHOD FOR ADMINISTRATION OF A SUBSTANCE

FIELD

The present subject matter is in the field of substance delivery systems.

BACKGROUND

Human diseases are frequently treated with substances that are intended to produce a therapeutic effect in said individuals. These substances are typically denoted with the terms "medicine", "intervention", "medicament", "medication", "drug", drug substance", "drug product" or "biologic." A medicament may be defined as a substance used to restore health or a substance used in the prevention or treatment of disease. It can refer to any substance intended for use in the diagnosis, cure, mitigation, treatment, or prevention of a disease.

Substances may be broadly drawn from any of a number of sources including natural products such as heparin, chemically synthesized agents such as small molecules; botanically derived molecules that are isolated from plants, fungi, and molds; biotherapeutic large macromolecules that may include vaccines, growth factors, immune modulators, and monoclonal antibodies as good substances derived from human blood and plasma; or genetic agents such as nucleic acids acid including gene therapies and sRNA treatments.

Such substances are typically administered by one of several alternative delivery routes including without limitation oral and parenteral (non-oral). Parenteral administration routes include methods of delivering substances into the body intending to sidestep the gastrointestinal tract. The routes may include rectal, sublingual, transbuccal, transpulmonary via inhalation or atomization, transalveolar, intramuscular, intravenous, subcutaneous, transdermal, intranasal, epidural, intrathecal and intraperitoneal.

These routes may also be referred to by standard abbreviations. For example, PO (per os) may be used for reference to oral administration; IV for intravenous administration; SC for subcutaneous administration; IM for intramuscular administration; IP for intraperitoneal administration; PR for per rectal administration; IN for intranasal administration; and INH for inhaled medications.

Pharmacokinetics is the process that describes how the body absorbs, distributes, metabolizes and excretes drug substances. The processes involved in drug metabolism are typically described according to the acronym LADME, which refers to liberation of drug from its carrier (if applicable), "A" is for absorption, "D" is for distribution, "M" is for metabolism and "E" is for excretion.

SUMMARY

The following embodiments and aspects thereof are described and illustrated in conjunction with systems, tools and methods which are meant to be exemplary and illustrative, not limiting in scope.

There is provided, in accordance with an embodiment, a system for administering a substance to a patient, the system including a reservoir for storing the substance, an administration apparatus configured to administer the substance to the patient, a pump for directing the substance from the reservoir to the delivery mechanism, a controller configured to operate the pump, a communication unit configured to communicate with one or more servers, one or more processors configured to receive data associated with patient characteristics, calculate a substance administration dose according to the data, determine a preferred substance administration process, and operate the pump to administer the substance to the patient.

In some cases, the processor is further configured to record patient data during and after substance administration to the patient and transmit the patient data to one or more servers.

In some cases, the administration apparatus is an inhalation or nasal delivery apparatus.

In some cases, the administration apparatus is an intravenous delivery apparatus.

In some cases, the system further includes a cartridge for storing the substance.

In some cases, the system further includes a memory, wherein the processor is further configured to store the patient data and administration data in the memory.

In some cases, the system further includes a user interface for receiving input from a user for the operation of the controller and to provide user information.

In some cases, the user interface enables the user to view information about the substance administration to the patient.

In some cases, the one or more processors receive one or more external physiological signals.

In some cases, both parent compounds and metabolites are delivered in parallel from two or more administration apparatuses.

In some cases, the processor is configured to execute a execute a real-time dynamic calculation (RTDC) module for dynamic flow rate data for substance administration.

In addition to the exemplary aspects and embodiments described above, further aspects and embodiments will become apparent by reference to the figures and by study of the following detailed description.

BRIEF DESCRIPTION OF THE FIGURES

Some non-limiting exemplary embodiments or features of the disclosed subject matter are illustrated in the following drawings.

Identical, duplicate, equivalent or similar structures, elements, or parts that appear in one or more drawings are generally labeled with the same reference numeral, optionally with an additional letter or letters to distinguish between similar entities or variants of entities, and may not be repeatedly labeled or described.

Figure 1:
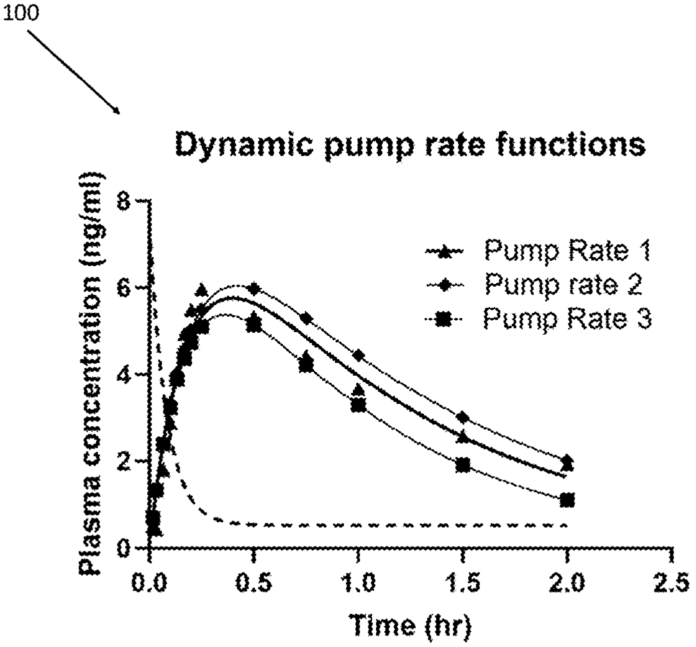

Dimensions of components and features shown in the figures are chosen for convenience or clarity of presentation and are not necessarily shown to scale or true perspective. For convenience or clarity, some elements or structures are not shown or shown only partially and/or with different perspectives or from different points of view.

References to previously presented elements are implied without necessarily further citing the drawing or description in which they appear.

FIG. 1 shows a chart of substance administration, according to certain exemplary embodiments; The dashed line shows the typical PK of a substance following IV administration without use of the present invention. The solid lines show exemplary PK profiles obtained based on exemplary embodiments of the present invention.

Figure 2:
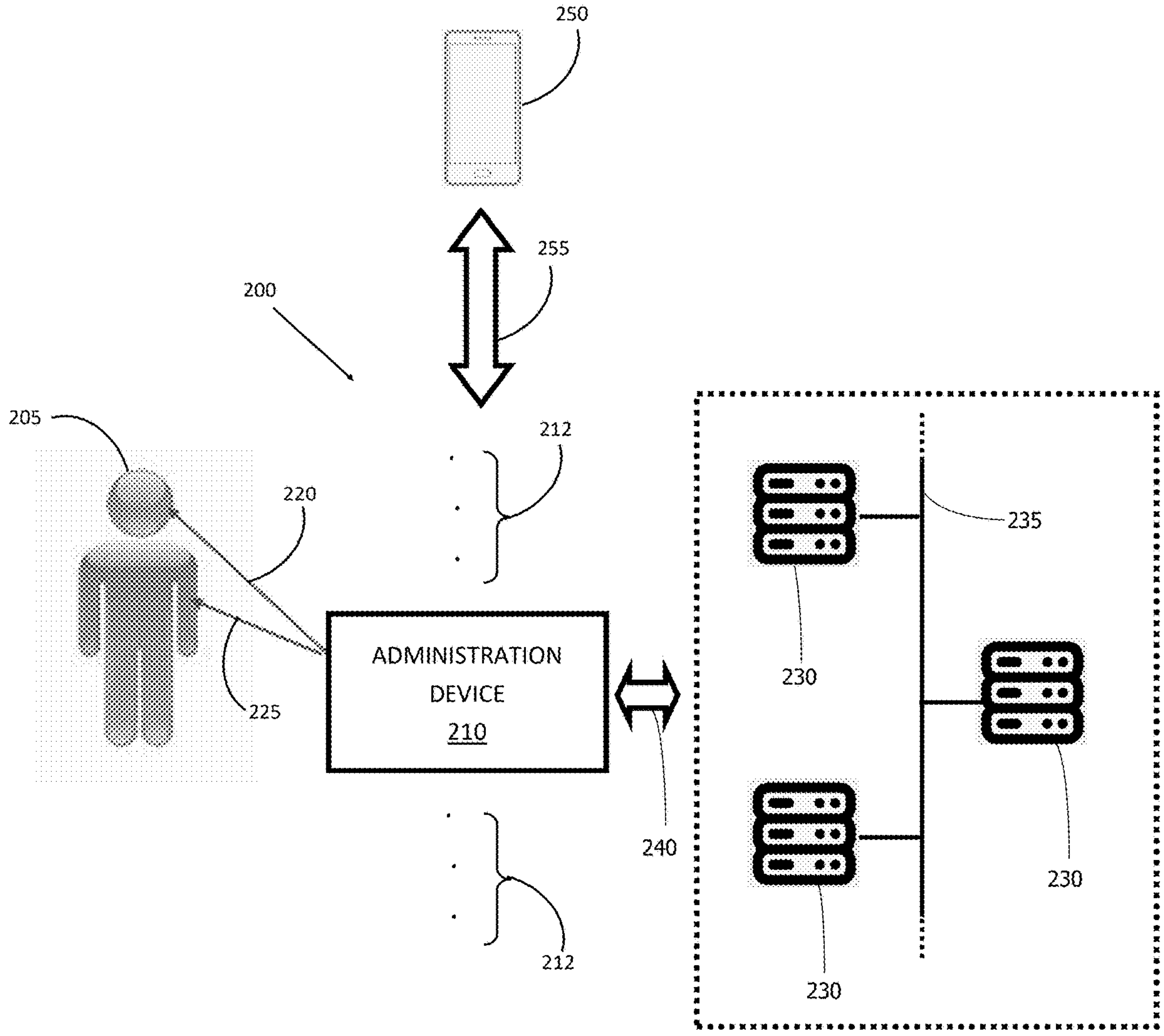
Figure 3A:
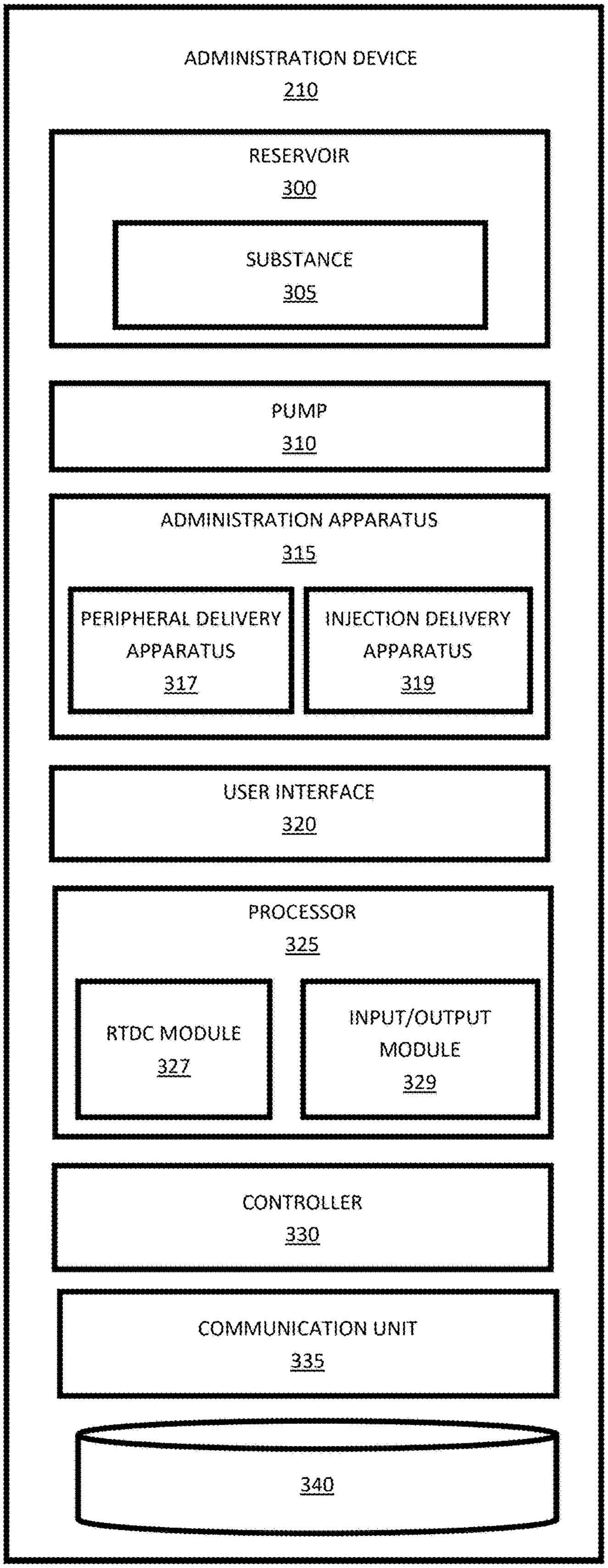
Figure 3B:
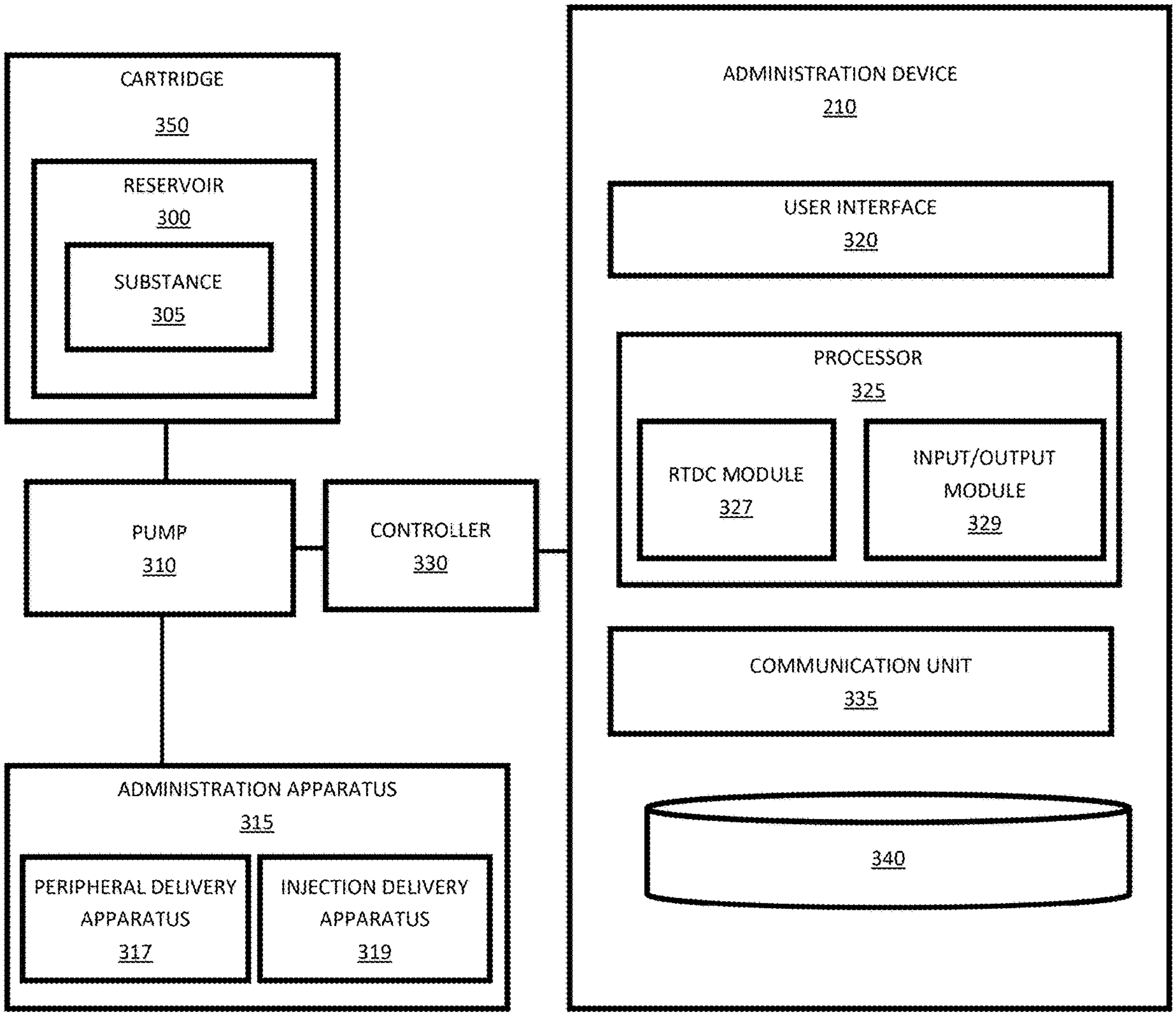
Figure 4:
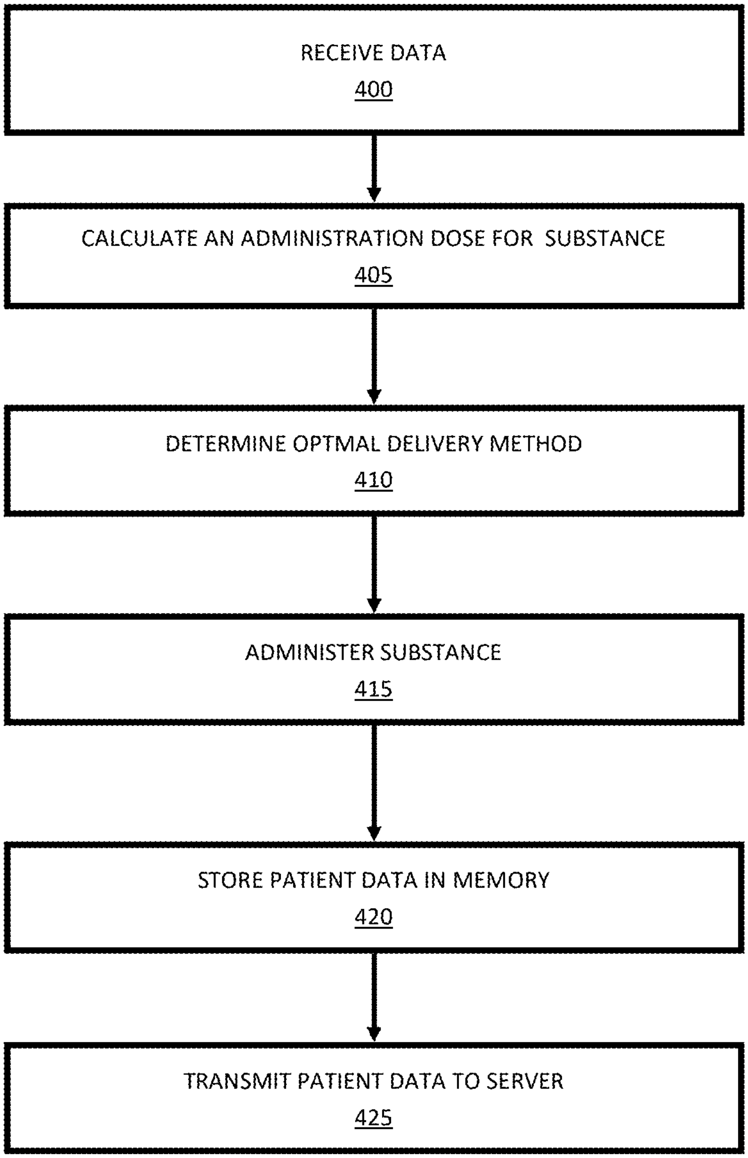

FIG. 2 is a schematic illustration of a system for administering a substance to a patient, according to certain exemplary embodiments;

FIGS. 3A-3B are schematic illustrations of the administration device of FIG. 1, according to certain exemplary embodiments; and, FIG. 4 outlines operations for administering a substance to a patient, according to certain exemplary embodiments.

DETAILED DESCRIPTION

Described herein is a system and a method for the administration of a substance, according to certain exemplary embodiments.

Following delivery, substances show a characteristic pharmacokinetic ("PK") profile characterized by measures and parameters such as fractional availability (bioavailability), maximum concentration in the blood ("Cmax"), time to maximum concentration ("Tmax"), minimum plasma concentration ("Cmin"), average plasma concentration over a specified interval of time ("CAV)",), the area under the blood concentration-time curve ("AUC"), the volume of distribution ("Vd"), half-life (½t time to eliminate 50% of the drug), clearance (CL, rate of substance elimination by all routes of elimination) and absorption and elimination rate constants (k values). In some conditions, both absorption and elimination may occur by multiple processes and lead to bi- or multi-phasic PK profiles.

PK characteristics of a substance are typically described mathematically using models often referred to as compartmental methods, which characterize the flow of a substance from the site of administration into the bloodstream and into other body compartments. Additional compartments are theoretical spaces and may include highly perfused organs such as the brain; liver; kidney; muscle and/or fat tissues, reproductive organs; cerebrospinal fluid; lymphatic fluid; or urine.

PK characteristics can be modeled using standard software packages such as MATLAB (Simbiology), Pheonix WinNonlin (Certara) or PKMP (Applied Pharmacokinetics Laboratory) to name a few of the many software packages available to modelers.

Single-compartment or multi-compartment models may be used depending on the drug substance's ADME properties. Following an initial peak in blood plasma concentration, the plasma concentration may show an initial rapid decrease representing a distribution of the drug from the bloodstream into body tissues, as well as a more gradual decrease representing hepatic metabolism and renal excretion.

With reference to FIG. 1, which shows a multi-compartment model 100, according to certain exemplary embodiments. This model assumes that substances can be administered either orally or parenterally. IV administration leads to the direct entry of virtually 100% of the substance into a central compartment. consisting of blood, tissues, and organs with rapid distribution of the substance. A second compartment, called a peripheral compartment, represents organs and tissues where the substance distributes at a slower rate. Equilibrium is achieved as the substance moves back and forth between the central and peripheral compartments.

Other forms of parenteral administration, such as IM, SC, and intra-articular are associated with only a fraction ("FR") of the dose being absorbed, which affects the bioavailability of the administered substance.

In addition, there may be a delay ("Dap") and rate constant ("kap") that describes the transit of the substance from the site of administration to the central compartment due to numerous physical-chemical, physiological, and formulation factors. The central compartment has a theoretical associated volume of distribution ("Vc") for the initial drug distribution and equilibration within the central compartment. The parameter tau (τ) may describe a dosing interval. The elimination half-life of a substance may be described as the inverse of the rate constant for elimination multiplied by 0.693 (i.e, the natural log of 2)

From the central compartment, the compound may be distributed into variable numbers of peripheral compartments, described numerically as compartments 1 . . . n. Common names for peripheral compartments include shallow and deep, the former being well-perfused with rapid distribution and the latter being poorly perfused with slower distribution. Each peripheral compartment in turn has an associated volume of distribution (Vp1 . . . . Vpn). The processes involved in the distribution from the central to the peripheral compartments may be described by the respective inter-compartment clearance rate (Q).

Substances administered orally may only be fractionally available (FRo, Fgut), reflecting their oral bioavailability ("BA"), which can range from 5% up to 95% for most commercial products. Compounds with low BA typically have a delayed absorption through the gut following dissolution from their delivery system, reflected in the delay (Dao) and absorption rate constant ("Kao"). Following absorption in the gut, they are taken up by the hepatoportal system. They are then metabolized in the liver leading to the appearance of variable numbers of metabolites, each of which is associated with a specific rate of metabolism and return to the central compartment directly from the liver or through renal re-absorption. The processes may be represented by rate constants such as Kmet.

Both the parent compound and metabolites are cleared from the central compartment primarily by urinary excretion, through processes denoted as CL and CLm, or through biliary excretion and further liver metabolism.

In some cases, single processes are involved in the absorption, distribution, metabolism, and elimination of substances, in which case single rate-constant equations can be used. In some cases, these lead to processes that can be described by a single exponential function. In other cases, multiple parallel processes may contribute to the ADME processes, leading to multi-exponential functions to describe the PK profile.

In some cases, the rate constants may be affected by individual factors such as height, weight, race, or ethnicity (intrinsic factors), or by prior history of substance use, smoking, co-medications, or other extrinsic factors that would be required to be adequately represented in a model as different rate constants across individuals.

In some cases, the metabolites may be therapeutically active and contribute to the overall beneficial effects of the compound. In some cases, the metabolites may be associated with unwanted side effects. In some cases, the metabolites may be inert.

The PK profile of a substance may be a critical factor in determining its therapeutic activity including both the desired and undesirable effects. For example, high Cmax levels may in some cases lead to a rapid beneficial effect, but in other cases may produce side effects that limit drug tolerability.

Thus, in some cases, it may be beneficial to deliver compounds rapidly, for example, as a single bolus for relief of acute pain. However, in other cases, it may be beneficial to prolong delivery to maximize therapeutic benefit while minimizing symptoms, especially for chronic disease conditions. Based upon compartmental models, drug delivery systems can also be optimized to maximize delivery of substances to desired targets in a given compartment, while minimizing delivery to undesired targets in other compartments. Bioavailability may be defined as the proportion of an administered drug dose that reaches the systemic circulation and indirectly influences the amount of drug that reaches its site of action.

A large number of compounds have been developed for oral administration, but must on occasion be administered parenterally, for example in the case of extreme nausea, vomiting, or dysfunction of the gastrointestinal system. For such compounds, it may be desirable to develop parenteral administration approaches that recapitulate the PK profile observed after oral administration.

Other compounds have been developed for administration via other routes of administration such as intranasally or by inhalation. Examples of compounds that may be delivered by intranasal administration without limitation include oxytocin, glucagon, cocaine, sufentanil, midazolam, lorazepam, hydromorphone, flumazenil, fentanyl, ketamine, S-ketamine, R-ketamine, ketorolac, morphine, midazolam, and naloxone.

Examples of CNS-related compounds that may be prescribed by inhalation and include without limitation loxapine, levodopa, apomorphine, fentanyl, ketamine, S-ketamine, R-ketamine, cannabis, cannabidiol, alprazolam, dihydroergotamine, and zaleplon.

In some cases, no adjustment may be required to equate PK profile across different modes of administration or different formulations of the same active ingredient. For example, in comparative studies, it has been shown that the PK properties of intranasal and subcutaneous naloxone were similar, permitting interchangeable use of the system. Similarly, dexmedetomidine has been shown to have a similar PK profile following delivery by intranasal atomization vs. intranasal drops.

Nevertheless, in both cases, both atomized and intranasal dexmedetomidine showed slower update kinetics relative to IV dexmedetomidine, suggesting that modifications in the administration rate of IV dexmedetomidine would be required to reproduce the PK profile of either atomized or intranasal versions.

An exemplary use of the present invention would be to reproduce the PK profile of a compound such as atomized or intranasal dexmedetomidine administration using targeted-controlled or dynamically adjusted intravenous infusion based upon real-time computer models. This could be accomplished, for example, by reduction of the total dose to compensate for the reduced bioavailability of the atomized and intranasal dexmedetomidine relative to the IV administration, as well as by continuous or continual modulation of the rate of IV dexmedetomidine administration to mimic the absorption kinetics of atomized or intranasal dexmedetomidine.

The PK properties following atomized or intranasal delivery would be considered the "native" properties (original or conventional route of administration) of the medicament to be delivered (i.e. dexmedetomidine), and IV administration would be considered the "desired" (alternative or optimized) route of administration. The system would permit transitioning from the PK of the native route of the medicament to the PK using the desired route of administration.

An additional exemplary embodiment would be to reproduce the PK properties and concentration-time profiles of intranasal S-ketamine, R-ketamine, or racemic ketamine using dynamically controlled IV administration. A third theoretical exemplary use would be to mimic the PK properties of intranasal S-ketamine, R-ketamine, or racemic ketamine using an inhaled formulation of those compounds.

Finally, for these examples, it may be beneficial to modulate the IV infusion flow rate continuously or continually based on calculated compartmental models to achieve specific PK profiles. For example, it may be beneficial to begin administration at a relatively increased flow rate that is then decreased over time for example exponentially to compensate for the initial saturation of fluid compartments. It may also be beneficial to begin administration at a relatively decreased flow rate that is then increased over time for example exponentially to minimize time-dependent variations in drug concentrations related to the drug's unique pharmacokinetic properties. In some cases, it may be beneficial to use multiphasic compartment models to achieve the desired drug exposure.

The system described herein uniquely permits interconversion among administration routes such that the PK profile associated with one route of administration such as oral, intranasal, or subcutaneous may be reproduced by a different route of administration such as intravenous, intramuscular, or inhalation administration. The system also makes use of compartmental modeling to achieve PK profiles that optimize drug dosing and achieve the desired therapeutic effect while minimizing drug side effects.

A preferred method for controlling the PK of an administered compound is through the use of a controlled flow system, such as an infusion pump. Such pumps are most commonly used to infuse substances intravenously. However, infusion pumps may also be used to deliver substances through other parenteral routes of administration.

A critical feature of controlled infusion systems is the ability to precisely adjust the rate of fluid flow at the outlet of the system, typically given in units such as milliliters/minute (mL/min) or per hour (mL/hr). The flow rate multiplied by the concentration of a substance in the infusion fluid typically denoted in milligrams per milliliter (mg/mL) will determine the rate of substance delivery for example in milligrams/minute (mg/min) or per hour (mg/hr).

The term "infusion rate" denotes the rate at which an injector-based system delivers a fluid into the central compartment of a human. In presently available controlled flow systems, such rates are typically either constant or are adjusted in a stepwise fashion over time. The term "dynamic rate of infusion" denotes a rate of infusion that changes systematically and continuously or continually over time in order to implement a preferred PK profile.

Examples of types of infusion systems without limitation include large-volume pumps, box pumps, peristaltic pumps, patient-controlled analgesia pumps, elastomeric pumps, syringe pumps, multi-channel pumps, volumetric pumps, ambulatory pumps, and gravity-controlled pumps.

Syringe pumps generally utilize a piston that is operated by a motor that advances the piston through a mechanical interface such as a drive screw or worm gear and may be electronically controlled or programmed in advance. In a syringe pump, a syringe of pre-specified size is typically attached firmly to the body of the pump for example by the use of a clamp or other type of syringe holder. The piston then drives the plunger at a pre-determined rate. The flow rate of the system is determined both by the diameter of the syringe and the rate of motion of the piston.

Peristaltic pumps generally use moving rollers or rotating "fingers" to compress silicone tubing containing the to-be-infused fluid. The rate of infusion may be automated and is monitored by a sensor that monitors the flow rate of the fluid through the tube and adjusts the rate of compression.

Presently available infusion systems are designed to administer fluids at a flow rate programmed in advance. If it is desired to change the flow rate, the new flow rate must be entered manually. Present infusion systems do not permit continuous manipulation of the flow rate according to a preset mathematical equation and compartmental model. Present infusion systems are thus incapable of practicing the present invention.

Injector-based systems may also be designed to take input from external devices to modulate the flow rate over time. The source of the feedback signal may be an external physiological measure such as pulse rate, blood pressure, or EEG. An example is an automated insulin pump which reacts to real-time monitoring of blood glucose and can automatically adjust the insulin delivery rate.

Another example, U.S. Pat. No. 2,888,922A describes a system in which the rate of drug administration varies in response to a bodily function that generates or is represented by an electrical signal. Such a signal, for example, may be an EEG. U.S. Pat. No. 7,833,213B2 describes a system in which the monitoring and drug delivery functions of the system are physically distinct. U.S. Pat. No. 10,537,677B2 describes a system in which EEG is used to calculate anesthetic depth and generate control signals based on the difference between the desired level of anesthetic depth and the observed level. This input is then used to regulate the flow rate of the injector system and adapt to the patient's needs. These disclosures are incorporated by reference.

Injector-based systems may also be designed to automate processes related to the calculation of infusion rate and for accurate recording of the precise dosage delivered. For example, U.S. Pat. No. 9,132,228B2 describes a system wherein a fluid cartridge device such as a prefilled syringe may contain one or more machine-readable indicators that indicate the identity and strength of the solution within the cartridge, and wherein the infusion device may be integrated to detect the machine-readable indicators and convey such (i.e. provide feedback) to an external device such as a computer in order to minimize errors in the administration of medications. information and to reduce the risk of over- or under-dosing information from this patent is hereby incorporated by reference.

FIG. 2 is a schematic illustration of a system 200 for administering a substance to a patient 205, according to certain exemplary embodiments. System 200 includes one or more administration devices 210, illustrated as one instance of an administration device 210, representing any number of administration devices 210, as indicated by dots 212. Administration device 210 is configured to administer the substance to patient 205 through preselected methods, such as intravenously, as schematically illustrated by arrow 225, or by inhalation, as schematically illustrated by arrow 220, and as further described herein in conjunction with FIGS. 3-4. System 200 includes one or more servers 230, illustrated as three instances of a database 230, representing any number of servers 230, as indicated by dashed line 235.

One or more administration devices 210 are connected or linked to servers 230 by any communication facility or facilities included in system 200 as schematically illustrated by arrow 240, which facilitates the data flow from one or more servers 230 to one or more administration devices 210. One or more servers 230 are configured to store data that facilitates accurate and effective substance administration to the patient 205 according to administration data stored in one or more servers 230.

In some embodiments, system 200 includes smart device 250 that facilitates remote control of administration device 210. For example, smart device 250 can be a smartphone, laptop, or the like. Smart device 250 is configured to communicate via wireless communications, as schematically illustrated by arrow 255. In some embodiments, system 200 would employ bar codes on the injector device and on the individual drug doses to reduce diversion liability and facilitate accurate tracking of administered medications.

In some cases, system 200 can reduce errors related to manual entry of flow rates into a substance delivery system.

In some cases, the errors will be related to the manual entry of flow rates relating to dynamic flow rates for substance administration.

FIG. 3 is a schematic illustration of administration device 210, according to certain exemplary embodiments.

Administration device 210 includes a reservoir 300 operative for storing a substance 305 to be administered to patient 205 (FIG. 2) and an administration apparatus 315 operative to administer substance 305 to patient 205.

Administration device 210 includes a pump 310 configured to pump substance 305 from reservoir 300 to administration apparatus 315.

Administration device 210 includes a user interface 320 configured to enable a user to input commands to administration device 210 and to receive output, such as visual and/or audio to provide information to the user about the substance administration to the patient 205 (FIG. 2).

In some embodiments, user interface 320 is configured to enable a user to input commands to control the operation of pump 310 thereby controlling the rate and dosage of substance 305 to patient 210.

Administration device 210 includes a processor 300 configured for executing operations for administrating substance 305 to patient 205. In some embodiments, processor 300 is configured to execute a real-time dynamic calculation (RTDC) module 327 that provides dynamic flow rate information to controller 330 and an input/output (IO) module 329 that facilitates programming of the desired characteristics of dynamic calculation module 327. In some embodiments, system 200 (FIG. 2) can include multiple administration devices.

Optional modules may provide remote control of administration device 210 for example through the internet, wireless communication, or the like. Remote modules can record additional information about patient 205 receiving substance 305, and can record data of the substance administration. In some embodiments, the modules can also interact directly with the clinical record of patient 205, for example, in one or more servers 230 or in a memory 340 of administration device 210.

In some embodiments, system 200 is configured to recapitulate the intranasal, transdermal or sublingual PK of substances 305 such as dexmedetomidine (patent EP3406247A1), dextromethorphan (U.S. Pat. No. 11,684,619B2), ketamine, S-ketamine, R-ketamine using administration routes such as intravenous, intramuscular, subcutaneous or inhalation routes.

Administration apparatus 315 includes an injection delivery apparatus 319 for infusion of substance 305 into a fluid-filled body compartment such as the venous, arterial, intramuscular, subcutaneous, or the like of patient 205. In some embodiments, where other routes of administration are implemented, such as intranasal or inhalation, administration device 210 includes a peripheral delivery apparatus 317. In some embodiments, peripheral delivery device 317 can be an inhaler, a face mask, a spray device, a nasal cannula, a nebulizer, a powder inhaler or the like.

For injection delivery apparatus 319, the size of an injector may be selected based on the target compartment. For example, for intravenous administration, needles between gauges of 14-23, 21-23, 24-29, and 25-32 millimeters may be appropriate for intravenous, intramuscular, intradermal, or subcutaneous injection, respectively. When administration is performed via peripheral administration through 317, the physical characteristics of the administration device will be configured to provide efficient absorption of substance 305 through the target mucosal surface or other route of administration.

In some embodiments, substance 305 may be delivered by peripheral delivery apparatus 317 in a vaporized form, for example, by a nebulizer, or in powder form, for example, by a powder inhaler. When a nebulizer is used, Substance 305 will be contained in Reservoir 300 in liquid form. When a powder is used, Substance 305 will be contained in Reservoir 300 in solid form. Critical factors affecting dry powder inhalation include blend uniformity, aerosol performance, and variability. Liquids can be administered through pressurized metered dose inhalers or nebulized or soft-mist aqueous formulations.

The use of nebulization as a delivery system is well-known in the field of pharmaceutical medicine and has been described in multiple publications. Examples of nebulization systems include jet nebulizers and soft mist inhalers, which utilize low-velocity sprays. Liquids may be converted to mists using ultrasonics, vibrating meshes, or other novel approaches. Substance 305 in liquid form can include water, aqueous solutions, suspensions, oils, or the like.

In some embodiments, substance 305 in a solid state can be converted into dry powders to aid in administration through processes such as lyophilization. Appropriate stabilizers and excipients may be included to promote stability and tolerability.

Pump 310 is configured to deliver substance 305 from reservoir 300 in a plurality of methods. For example, for liquids, pump 310 can be a large-volume pump, a box pump, a peristaltic pump, a patient-controlled analgesia pump, an elastomeric pump, a syringe pump, a multi-channel pump, a volumetric pump, an ambulatory pump, a gravity-controlled pump, or the like.

Administration device 210 includes a controller 330, which is configured to modulate the rate at which substance 305 is administered to patient 205. For example, controller 330 regulates the operation of pump 310. Controller 330 may be configured to operate either electrically or mechanically.

For example, when pump 315 is a syringe pump, the signal from controller 330 can control the liquid flow rate from the pump reservoir 300 to administration apparatus 315 via an analog or digital signal. In the case of analog input, the voltage, frequency, or other properties of a continuously varying signal can be used to modulate current flow. In the case of a digital signal, the desired flow rate can be encoded dynamically using a series of bits that create a digital number. The number is varied continually over time and encoded in the pattern of bits. The intervals at which the bits are varied can range from microseconds to minutes. In preferred implementations, the intervals will range from approx. 100 milliseconds to approximately 10 seconds, corresponding to refresh rates within a range of 0.1 to 10 Hertz ("Hz").

In some embodiments, peripheral delivery apparatus 317 or other complex administration apparatus, the controller signal can be delivered directly to the administration apparatus 315. For example, peripheral delivery apparatus 317 can provide a signal to modulate the airflow continuously or continually. In some cases, an ultrasonic or vibrating mesh system (not shown) can control the rate or strength of vibration.

RTDC module 327 can provide the signal that regulates controller 330. The function of RTDC module 327 is to interconvert between native PK characteristics of one form of administration and the desired PK characteristics for delivery of the specific substance.

In some embodiments, the rate of delivery through the administration is determined according to a ratio of absorption time constants between the native and the desired route of administration. In other cases, more complex functions may be needed based upon alterations in elimination rates, compartmental distributions, and other factors, and multi-exponential solutions will be required.

In some embodiments, RTDC module 327 calculates a dynamic rate at which substance 305 needs to be delivered via the administration apparatus 315 and provides the appropriate control signal to pump 310. The formula that determines the dynamic rate is programmed into an operating system of administration device 210, which will then perform real-time calculations based on the formula.

In other embodiments, a look-up system (not shown) is utilized, which provides a dynamic signal that is encoded in advance based upon external calculation, and the results of the calculation are uploaded into the system. RTDC module 327 will then transmit the precalculated values dynamically to pump 310. In some embodiments, RTDC module 327 can use values precalculated based upon mean parameters calculated across a general population based on data, which can be received via communication unit 335, which receives the data from one or more servers 230 (FIG. 2). In some embodiments, values are calculated based upon characteristics of patient 205.

For example, in a case where intravenous ("IV") administration is used to emulate oral or intranasal administration, the total dose of the delivered medication will be reduced to account for the differential bioavailability between the routes. In addition, the rate of flow will be altered dynamically based on the relative absorption and elimination rates of the differential routes of administration.

For example, when substance administration is through inhalation, similar rate constants can be observed across system 200, but the bioavailability may differ as a function of patient characteristics such as respiratory volume, or the like. In such exemplary cases, dynamic correction may be required for differences in bioavailability, which may further vary over the duration of the administration time.

In some embodiments, the function used to equate system 200 is calculated based on relative LADME models.

In some embodiments, the functions are established by direct experimentation on humans.

In other embodiments, both the parent compounds and metabolites of substance 305 are administered to equate concentrations of both the parent compounds and metabolites across the routes of delivery. In some embodiments, parallel administration devices 210 administer the parent compound and metabolites separately. In some embodiments, the real-time dynamic control (RTDC) module would calculate the needed flow rate continuously and control would be via an analog feedback signal that would permit continuous modulation of flow rate to the flow actuators.

In some embodiments, RTDC module 327 would calculate the needed flow rate at discrete, but brief intervals, and would relay the adjusted flow rate to the flow actuator. The intervals could be in the range of 0.1-100 sec, for example, 0.1 sec, 0.5 sec, 1 sec, 5 sec, 10 sec, 50 sec, 100 sec. Intermediate values are also possible. In a preferred embodiment, the real-time interconversion module would adjust flow rates every ~10 sec.

User interface 320 is configured to enable the user to enter the information needed for the RTDC module 327 to perform the calculations required to provide the dynamic control signal to pump 310. The input of user interface 320 can be by mechanical systems such as knobs or thumbwheel switches, or computer interface via connections such as USB, Wifi, Bluetooth or the like.

In some embodiments, outputs are provided to allow external capture of the control signal output from RTDC module 327 to controller 330. In some embodiments, the external control signal would be captured by system 200 and included in an external quality control system with fall-safe attributes such as line obstructions, empty reservoirs or misuse by the individual patient (not shown).

In some embodiments, the inputs provide information on a specific substance to be administered, along with its LADME characteristics using the available delivery routes, such as IV or nasal. In other embodiments, the LADME characteristics are stored in memory 340 and only the identity of substance 305 is required. In some embodiments, patient characteristics relative to LADME calculations are provided via user interface 320. In some embodiments, patient characteristics can include age, sex, body weight, height, ethnicity, race or the like.

In some embodiments, administration device 210 can receive four inputs, for example a desired dose to be delivered, a duration over which the dose is delivered, a rate constant for the route of administration to be emulated, and a rate constant for the route of administration to be used for the emulation.

In some embodiments, additional signals can be integrated into system 200. For example, system 200 requires remote enablement by an external monitor to ensure correct operation and safe use of administration device 210.

In some embodiments, administration device 210 links information about patient 205 and personnel supervising the administration with the substance administration to facilitate accurate record keeping. In some embodiments, this information is entered directly into an appropriate data repository such as an electronic medical record in one or more servers 230. In some embodiments, personnel operating administration device 210 are prompted to enter patient identifying information such as name, identification number, patient number, or the like.

In some embodiments, a cartridge containing the to-be-injected substance would contain a machine-readable indicator such as a bar or QR code, which would permit the system to determine key features of the to-be-injected substance including chemical composition, concentration, volume, and flow rate. In some embodiments, the information would be provided to the user through a human-compatible interface such as a monitor or printer. In some embodiments, the information would be entered directly into an appropriate data base such as an electronic medical record. In some embodiments, information from the machine-readable indicator would be input into the RTDC, thereby bypassing the need for user input and creating efficient clinical uptake.

FIG. 3B is a second embodiment of administration device 210, with reservoir 300, pump 310 and controller 330 can be external to administration device 210 thereby allowing administration device 210 being remote from the administration location for substance 315, according to certain exemplary embodiments. Administration device 210 can include a cartridge 350 that can be in fluid communication with pump 310.

FIG. 4 outlines operations performed by administration device 210 (FIG. 2) for administering substance 305 (FIG. 3A) to patient 205 (FIG. 2), according to certain exemplary embodiments. In operation 400, administration device 210 receives data associated with substance administration to patient 205. The data associated with substance administration can include patient medical data, data associated with patients having similar characteristics of patient 205 and data associated with substance 305. The data can be received from user interface 320 (FIG. 3A), from communication unit 335 (FIG. 3A). In some cases, substance information is collected from cartridge 350 (FIG. 3B), which when connected to pump 310 (FIGS. 3A-3B) can be read by a sensor for identifying, for example, a QR code, barcode, RFID chip, or the like by processor 325 (FIG. 3A).

In operation 405, administration device 215 calculates a substance dose for administration. In some embodiments, administration device 215 can utilize artificial intelligence and machine learning to analyze patient characteristics received from one or more servers 230 (FIG. 2) along with patient characteristics to build a patient profile for a preferred dose and delivery of substance 315 to patient 205.

In operation 410, administration device 215 determines an optimal delivery of substance 315. For example, administration device 215 is configured to determine whether substance 315 should be administered through IV or through nasal delivery.

In operation 415, administration device 215 administers substance 315 to patient, as described herein in conjunction with FIGS. 3A-3B.

In operation 415, administration device 215 records patient data about patient 205 during and after administration of substance 315.

In operation 420, administration device 215 stores the patient data in memory 340 (FIG. 3A).

In operation 420, administration device 215 transmits the patient data to one or more servers 230 for storage and future use in other medical procedures.

EXAMPLES

Example 1: Emulation of Intranasal Naloxone Using IV Administration

An example of how system 200 can be applied in clinical situations is based on data comparing intravenous, intramuscular, and inhaled naloxone for outpatient use.

Naloxone is presently FDA approved for treatment of opioid overdose. Recent administration devices have also been approved for use by laypersons outside of a supervised medical scenario. These include an auto-injector for intramuscular ("IM") or subcutaneous ("SC") administration for use with a naloxone dose of 0.4 or 2 mg, and an intranasal ("IN") spray with a concentrated naloxone dose of 2 or 4 mg in 0.1 ml of solution.

The pharmacokinetics of blood levels following IN administration are prolonged relative to those of IV, IM or SC administration. In some circumstances, it may be beneficial to emulate the longer PK of intranasal administration using IV, IM or SC administration.

When administered IV, naloxone has a $T_{max}$ of <5 min. IM/SC injection show $T_{max}$ values in the range of 12.6-15 min. IN administration is associated with a $T_{max}$ of 18-30 min. The bioavailability of the IM/SC dose is considered to be 98.3%. The bioavailability of naloxone administered by nasal spray is considered to be in the range of 40-55%.

Based on data provided by the PK profile of IN naloxone could be fit using a combined one-phase association (also referred to drug-receptor binding) and dissociation (also referred to as drug-receptor unbinding) model of the form:

$$\text{Plasma Concentration}=C_{max}\times(1-e^{-k_{abs}\times t})\times(e^{-k_{elim}}\times t),$$

where e represent the exponent to the indicated power, t represents time, the parameter $k_{abs}$ models the absorption of naloxone after IN administration expressed in units of inverse time and $k_{elim}$ models the elimination of naloxone over time after administration.

Across IN doses of 1, 2 and 4 mg, the $k_{abs}$ value was best fit using a value of 4.47/hr, corresponding to an absorption half-life of 9.30 min. The elimination rate-constant also did not differ significantly across doses, with a mean value of 0.82/hr, corresponding to a half-life of 50.9 min. $C_{max}$ values for the conditions were 2.10, 4.30, and 10.10 ng/ml, respectively. The goodness of fit ("R2"), which explains variability in the data, for all of the simulations was greater than 0.9, that is, at least 90% of the statistical variance is explained by the statistical mode.

Following intravenous administration of 0.4 mg IV, the plasma concentration could be fit using a single elimination model of the form:

$$\text{Plasma Concentration}=C_{max}\times e^{-k_{elim}\times t}.$$

The best-fit value for K was 12.16/hr, corresponding a half-life of 3.4 min. The goodness of fit for the model was greater than 0.97.

Based upon these values, plasma values corresponding to those achieved following 0.4 mg IN administration could simply and efficiently be produced by administering IV naloxone using a rate curve shown in FIG. 1, wherein the administration rate of naloxone is adjusted continuously over time to emulate the PK curve observed following IN naloxone.

Given the much faster elimination kinetics shown following IV versus IN administration, no adjustment of the IV rate relative to the naloxone PK curve is needed (FIG. 1, Pump Rate 1). However, in some scenarios the elimination rate will increase following sustained administration, necessitating an increased administration rate (Pump Rate 2), whereas in other scenarios it will decrease, necessitating a decrease administration rate (Pump Rate 3).

Final selection of the model will depend upon the parallel evaluation of the modeled function relative to native administration. Once the resultant model is programmed into RTDC module 327, system 200 will be able to emulate the PK profile of IN naloxone administration using IV administration.

Example 2: Emulation of Intranasal Dexmedetomidine Using IV Administration

Dexmedetomidine is a highly selective alpha2 adrenergic receptor antagonist that produces dose dependent sedation with no respiratory depression, the relative pharmacokinetics of IN administration by either drops or atomizer relative to IV administration.

PK time data can be fit using a 2-compartment disposition model, with transit intranasal absorption and clearance driven by cardiac output using the well-stirred liver model.

Disposition was similar following intravenous and intranasal administration. Intranasal administration by atomizer and drops was associated with absorption rate constants (kabs) of 0.857/hr and 0.725/hr, respectively. The delay in uptake was modeled using a mean transit time of 0.176 hr and 0.163 hr for atomizer and drops, respectively. Intranasal bioavailability was estimate to be ~40% for both atomization and drops.

Using these parameters, IV administration could be used to emulate IN administration by first, decreasing the dose to ~0.4 of the IN dose, including a start delay corresponding to the desired mean transit time and administering the drug in accordance with a one-parameter association model of the form:

$$\text{Dynamic Rate}=[\text{max dose}]\times(1-e^{(-k_{abs}\times t)}$$

As with other models, adjustment may be needed based upon empirical comparison, including visual fit of PK profiles, of the native and emulated doses.

Example 3: Emulation of Intranasal S-Ketamine Using Intravenous Esketamine

A third example of application of system 200 comes from consideration of the PK of S-ketamine (esketamine) following IN administration. Esketamine is currently approved for the treatment of depression at an initial starting dose of 56-84 mg biweekly for 4 weeks during induction, followed by 56-84 mg weekly during weeks 5-8. The compound is administered in puffs of 28 mg each. For administration of 56 mg, two puffs are delivered 5 minutes apart. For 84 mg, 3 puffs are delivered with intervals of 5 min between puffs. The volume of delivery for each puff is 0.2 mL.

The PK of intranasal S-ketamine has been extensively reviewed.

The uptake of esketamine following IN administration was modeled using a 3-compartment model, with one central compartment that maintained equilibrium with two peripheral compartments, that is, shallow and deep peripheral compartments. Several parameters were needed to model the IN PK relative to IV PK.

First, IN administration leads to absorption via both the nasal epithelium and the gut when some of the dose is swallowed. Based upon the models, ~54% of the dose is absorbed through the nasal cavity while the remaining 46% is swallowed. The percentage that is swallowed undergoes first-pass metabolism in the liver such that only 18.6% reaches the systemic circulation. The absolute bioavailability of intranasal esketamine is ~50%.

The fraction that is absorbed through the nasal mucosa equilibrates into the central compartment with an absorption time constant (ka, n) of 2.93 L/h, leading to a mean absorption time of 20 min. Absorption through the gut is slower with a mean ka of 0.97 L/h, leading to a mean absorption time of 2.02 hr.

Cmax and AUC values are larger for noresketamine than ketamine following IN administration. In Caucasians 18-60 years of age, Cmax values of 43.8, 72.5, and 101 are observed for esketamine following 28, 56 and 84 mg administration, as compared to values of 59.1, 119.7, and 180 for noresketamine. AUC0-24 h values of 147.3, 254.7 and 362.2 are observed for esketamine, as compared to 274.4, 516.3 and 758 for noresketamine. Values differ somewhat by age and race.

These ADME parameters permit modeling of the dynamic IV dosing required to recapitulate the IN PK, for example by continuously modulating the rate of IV administration to emulate the exponential absorption curve associated with the mean or individual ka, n value. This device uniquely permits implementation of the continuous functions needed to translate across routes of administration provided by system 200.

Example 4: Emulation of Inhaled Esketamine Using Intravenous Esketamine

Ketamine has been shown to be absorbed by inhalation administration. Absorption of drugs by inhalation across the lungs is generally faster than by intranasal administration due to the larger surface area and vascular bed of the pulmonary versus nasal mucosa.

In a study, esketamine was administered at doses of 25, 50 and 100 mg intranasally and PK was compared to that observed following an intravenous dose of 20 mg. Administration was via a commercial nebulizer system that employed a high-frequency vibrating mesh. Arterial concentrations of esketamine and noresketamine were obtained.

$T_{max}$ values for inhalation of 0.35, 0.5 and 0.7 mg/kg doses were 22, 15 and 25 min, respectively. $C_{max}$ values were 128, 180 and 227 ng/ml or approximately dose proportional. $T_{max}$ values for S-norketamine were 63, 48 and 41 min. $C_{max}$ values were 52, 97, and 153 ng/ml, respectively, for the three doses.

The relative PK characteristics of esketamine applied by INH versus IV infusion were fit with a multicompartment model that was shared across routes of administration. However, for INH administration 3 parameters were required to account for the differential absorption characteristics: F, corresponding to the extent of bioavailability; ϕ, corresponding to the proportion of esketamine that transits directly to the main central compartment; and k, which describes the rate constant between the slow compartment and the main central compartment.

The modeled F value across INH doses was 0.70, reflecting 70% bioavailability following INH administration. In addition, a dose-dependent reduction in bioavailability of 20% was observed at the higher doses.

In the population, 70% of the dose was directly absorbed through the alveoli, whereas 30% traveled via a slower pathway that potentially included lung, GI or oropharyngeal absorption. The rate constant of the slow ketamine transit was 0.05/min, corresponding to a half-life of 13 min. 78% of esketamine was metabolized to noresketamine.

Based upon these parameters, the INH absorption pattern could be emulated using IV administration by reduction of the IV dose to 70% of the inhaled dose, use of an initial bolus to emulate the rapid absorption path and adjustment of the flow rate to emulate the slow path of equilibration between compartments.

Parameters for these pathways can be determined using standard PK modeling such as shown in Jonkman et al. and can be adjusted based upon parallel in vivo data collection using standard approaches.

Example 5: Emulation of Intranasal Esketamine Using Inhaled Esketamine

No studies have yet evaluated the comparative PK profile of intranasal and inhaled esketamine within the same individuals. Nevertheless, the above examples demonstrate that absorption is more rapid following INH versus IN esketamine, permitting calculation of the dynamic administration levels needed to translate across routes of administration.

Current devices for INH administration, such as nebulizers, may provide flow rates of up to 0.25 ml/min. Esketamine is currently formulated in a preparation containing 28 mg/0.2 mL, corresponding to 140 mg/ml. Thus, current devices permit delivery of up to 35 mg/min, which exceeds the current IN dose of 28 mg/5 min (5.6 ml/min).

Dynamic modulation of dosing can be accomplished by variation both of the nebulization rate and the concentration of the fluid analogous to the dose size. Metabolites such as noresketamine can be added, if needed, to equate across parent/metabolite ratios. Combined treatment with additional oral or intravenous administration can be used to more formally equate across dose levels. This device uniquely permits the available PK data to be used to allow dose emulation across routes of administration.

Example 6: Biomarker-Based Regulation of Infusion Rates

Medeiros et al., Personalized use of ketamine and esketamine for treatment-resistant depression, Transl. Psychiatry 14:481, 2024 describe the potential use of biomarkers to optimize ketamine delivery. Gamma power of the ongoing electroencephalogram has broad utility in that EEG is a widely available and portable modality. Changes in gamma power have been observed in relationship to ketamine infusion and clinical response. In an embodiment of this invention, EEG measures obtained simultaneously with the infusion would be used to dynamically regulate the PK parameters related to dose administration, thereby optimizing ketamine administration.

In the context of some embodiments of the present disclosure, by way of example and without limiting, terms such as ‘operating’ or ‘executing’ also imply capabilities, such as ‘operable’ or ‘executable’, respectively.

Conjugated terms such as, by way of example, ‘a thing property’ implies a property of the thing, unless otherwise clearly evident from the context thereof.

The terms ‘processor’ or ‘computer’, or system thereof, are used herein as the ordinary context of the art, such as a general-purpose processor or a microprocessor, RISC processor, or DSP, possibly comprising additional elements such as memory or communication ports. Optionally or additionally, the terms ‘processor’ or ‘computer’ or derivatives thereof denote an apparatus that is capable of carrying out a provided or an incorporated program and/or is capable of controlling and/or accessing data storage apparatus and/or other apparatus such as input and output ports. The terms ‘processor’ or ‘computer’ denote also a plurality of processors or computers connected, and/or linked and/or otherwise communicating, possibly sharing one or more other resources such as a memory.

The terms ‘software’, ‘program’, ‘software procedure’ or ‘procedure’ or ‘software code’ or ‘code’ or ‘application’ may be used interchangeably according to the context thereof, and denote one or more instructions or directives or circuitry for performing a sequence of operations that generally represent an algorithm and/or other process or method. The program is stored in or on a medium such as RAM, ROM, or disk, or embedded in a circuitry accessible and executable by an apparatus such as a processor or other circuitry.

The processor and program may constitute the same apparatus, at least partially, such as an array of electronic gates, such as FPGA or ASIC, designed to perform a programmed sequence of operations, optionally comprising or linked with a processor or other circuitry.

The term computerized apparatus or a computerized system or a similar term denotes an apparatus comprising one or more processors operable or operating according to one or more programs.

As used herein, without limiting, a module represents a part of a system, such as a part of a program operating or interacting with one or more other parts on the same unit or on a different unit, or an electronic component or assembly for interacting with one or more other components.

As used herein, without limiting, a process represents a collection of operations for achieving a certain objective or an outcome.

As used herein, the term 'server' denotes a computerized apparatus providing data and/or operational service or services to one or more other apparatuses.

The term 'configuring' and/or 'adapting' for an objective, or a variation thereof, implies using at least a software and/or electronic circuit and/or auxiliary apparatus designed and/or implemented and/or operable or operative to achieve the objective.

A device storing and/or comprising a program and/or data constitutes an article of manufacture. Unless otherwise specified, the program and/or data are stored in or on a non-transitory medium.

In case electrical or electronic equipment is disclosed it is assumed that an appropriate power supply is used for the operation thereof.

The flowchart and block diagrams illustrate architecture, functionality or an operation of possible implementations of systems, methods and computer program products according to various embodiments of the present disclosed subject matter. In this regard, each block in the flowchart or block diagrams may represent a module, segment, or portion of program code, which comprises one or more executable instructions for implementing the specified logical function (s). It should also be noted that, in some alternative implementations, illustrated or described operations may occur in a different order or in combination or as concurrent operations instead of sequential operations to achieve the same or equivalent effect.

The corresponding structures, materials, acts, and equivalents of all means or step plus function elements in the claims below are intended to include any structure, material, or act for performing the function in combination with other claimed elements as specifically claimed. As used herein, the singular forms "a", "an" and "the" are intended to include the plural forms as well, unless the context clearly indicates otherwise.

It will be further understood that the terms "comprises" and/or "comprising" and/or "having" and/or "includes" and/or "including" when used in this specification, specify the presence of stated features, integers, steps, operations, elements, and/or components, but do not preclude the presence or addition of one or more other features, integers, steps, operations, elements, components, and/or groups thereof.

As used herein the term "configuring" and/or 'adapting' for an objective, or a variation thereof, implies using materials and/or components in a manner designed for and/or implemented and/or operable or operative to achieve the objective.

Unless otherwise specified, the terms 'about' and/or 'close' and/or "substantially" with respect to a magnitude or a numerical value imply within an inclusive range of −10% to +10% of the respective magnitude or value.

Unless otherwise specified, the terms 'about' and/or 'close' and/or "substantially" with respect to a dimension or extent, such as length, imply within an inclusive range of −10% to +10% of the respective dimension or extent.

Unless otherwise specified, the terms 'about' or 'close' or "substantially" imply at or in a region of, or close to a location or a part of an object relative to other parts or regions of the object.

When a range of values is recited, it is merely for convenience or brevity and includes all the possible sub-ranges as well as individual numerical values within and about the boundary of that range. Any numeric value, unless otherwise specified, includes also practical close values enabling an embodiment or a method, and integral values do not exclude fractional values. A sub-range of values and practically close values should be considered as specifically disclosed values.

As used herein, ellipsis ( . . . ) between two entities or values denotes an inclusive range of entities or values, respectively. For example, A . . . Z implies all the letters from A to Z, inclusively.

The terminology used herein should not be understood as limiting, unless otherwise specified, and is for the purpose of describing particular embodiments only and is not intended to be limiting of the disclosed subject matter. While certain embodiments of the disclosed subject matter have been illustrated and described, it will be clear that the disclosure is not limited to the embodiments described herein. Numerous modifications, changes, variations, substitutions and equivalents are not precluded.

Terms in the claims that follow should be interpreted, without limiting, as characterized or described in the specification.

The invention claimed is:

1. A system for administering a substance to a patient, the system comprising:
- a reservoir for storing the substance;
- an administration apparatus configured to administer the substance to the patient;
- a pump for directing the substance from the reservoir to the delivery mechanism;
- a controller configured to operate the pump;
- a communication unit configured to communicate with at least one server; and,
- at least one processor configured to:
  - receive data associated with patient characteristics;
  - execute a real-time dynamic calculation ("RTDC") module for dynamic flow rate data for substance administration;
  - calculate a substance administration dose according to the data;
  - determine a preferred substance administration process; and
  - operate the pump to administer the substance to the patient.

2. The system according to claim 1, wherein the processor is further configured to:
- record patient data during and after substance administration to the patient; and,
- transmit the patient data to the at least one server.

3. The system according to claim 2, further comprising a memory, wherein the processor is further configured to store the patient data and administration data in the memory.

4. The system according to claim 1, wherein the administration apparatus is an inhalation or peripheral delivery apparatus.

5. The system according to claim 1, wherein the administration apparatus is an intravenous, intramuscular or subcutaneous delivery apparatus.

6. The system according to claim 1, further comprising a cartridge for storing the substance.

7. The system according to claim 1, further comprises a user interface for receiving input from a user for operation of the controller and to provide user information.

8. The system according to claim 7, wherein the user interface enables the user to view information about the substance administration to the patient.

9. The system according to claim 1, wherein at least one processor receives at least one external physiological signal.

10. The system according to claim 1, wherein both parent compounds and metabolites are delivered in parallel from at least two administration apparatuses.

* * * * *